United States Patent [19]

Salahuddin et al.

[11] Patent Number: 5,753,490
[45] Date of Patent: May 19, 1998

[54] RECOMBINANT HIV AND MODIFIED PACKAGING CELLS AND METHOD FOR TREATING ACQUIRED IMMUNE DEFICIENCY SYNDROME

[75] Inventors: Syed Zaki Salahuddin, Pasadena; Nickolas Chelyapov, Los Angeles, both of Calif.

[73] Assignee: Clinical Technologies, Inc., Pacific Palisades, Calif.

[21] Appl. No.: 563,597

[22] Filed: Nov. 28, 1995

[51] Int. Cl.$^6$ .............. C12N 7/00; C12N 7/01; C12N 7/02; C12N 7/04
[52] U.S. Cl. .............. 435/235.1; 435/236; 435/239; 435/172.3; 435/320.1; 514/44
[58] Field of Search .............. 435/320.1, 240.2, 435/172.3, 235.1, 236, 239; 514/44, 2, 45; 424/43.21

[56] References Cited

U.S. PATENT DOCUMENTS

| | | | |
|---|---|---|---|
| 5,149,529 | 9/1992 | Ho et al. | 424/88 |
| 5,171,568 | 12/1992 | Burke et al. | 424/89 |
| 5,244,792 | 9/1993 | Burke et al. | 435/69.3 |
| 5,306,631 | 4/1994 | Harrison et al. | 435/172.3 |
| 5,399,346 | 3/1995 | Anderson et al. | 424/93.21 |
| 5,428,143 | 6/1995 | Berger et al. | 536/23.4 |

OTHER PUBLICATIONS

Orkin et al., NIH Gene Therapy Meeting. Dec. 7, 1995.
Chenciner et al., Res. Virol., 146:171–178, 1995.
Dropulic et al., Human Gene Therapy, 5:927–939, 1994.
Gilboa et al., Trends in Genetics, 10(4):139–144, 1994.
Buchschacher et al., Journal of Virology, 66(5):2731–2739, 1992.
Brady et al., PNAS USA, 91:365–369,1994.
Martin A. Nowak, Andrew J. McMichael "How HIV Defeats the Immune System," *Scientific American*: Aug. 1995 pp. 58–65.
J. Cohen "Differences in HIV Strains May Underlie Disease Patterns," *Science:* v.270, Oct. 6, 1995: pp. 30–31.
George W. Nelson and Alan S. Perelson "Modeling Defective Interfering Virus Therapy for AIDS: Conditions for DIV Survival," *Mathematical Bioscience*,v.125 (1995): pp. 127–153.
J. Cohen "How Can HIV Replication Be Controlled," Science, v.260, May 28, 1993: p. 1257.
J. Cohen "What Causes Immune System Collapse Seen in AIDS?" Science, v.260, May 28, 1993: p. 1256.
J. Cohen "Can Combination Therapy Overcome Drug Resistance?" Science, v.260, May 28, 1993: p. 1258.
Lawrence M. Fisher "The Stuff of Dreams Nears Reality" The New York Times. Jun. 1, 1995: C1.
J. Cohen "Can One Type of HIV Protect Against Another Type?" Science, v.268, Jun. 16, 1995. p. 1566.

Karin Travers, et al. "Natural Protection Against HIV–1 Infection Provided by HIV–2," Science, v.268, Jun. 16, 1995. pp. 1612–1615.
J. Cohen "AIDS Mood Upbeat–For a Change" Science, v.267, Feb. 17, 1995. p. 959.
Rebecca A. Spence et al. "Mechanism of Inhibition of HIV–1 Reverse Transcriptase by Nonnucleoside Inhibitors" Science, v.267, Feb. 17, 1995. pp. 988–993.
J. Cohen "High Turnover of HIV in Blood Revealed by New Studies" Science, v.267, Jan. 13, 1995. p. 179.
William E. Paul "Reexamining AIDS Research Priorities" *Science*, v.267, Feb. 3, 1995. pp. 633–636.
Mariano A. Garcia–Blanco and Bryan R. Cullen "Molecular Basis of Latency in Pathogenic Human Viruses" *Science* v.254, Nov. 8, 1991. pp. 815–820.
John M. Coffin "HIV Population Dynamics in Vivo: Implications for Genetic Variation, Pathogenesis, and Therapy" *Science* v.267, Jan. 27, 1995. pp. 483–489.
S.L. McKnight and E.R. Grace "Expression of the herpes thymidine kinase gene in *Xenopus laevis* oocytes: an essay for the study of deletion mutants constructed in vitro" Nucleic Acid.
R. Shibata et al. "Comparative studies on tat mutants of three primate lentiviruses" Acrhice of Virology, v.114. pp. 243–250 (1990).

(List continued on next page.)

*Primary Examiner*—Jasemine C. Chambers
*Assistant Examiner*—Deborah J. R. Clark
*Attorney, Agent, or Firm*—Blakely, Sokoloff, Taylor & Zafman

[57] ABSTRACT

A recombinant human immunodeficiency virus (rHIV) and recombinant mammalian cell-line (packaging systems) and a method for treating infection of cells by human immuneodeficiency virus HIV. rHIV, such as rHIV-1, comprises of a gene construction which includes a foreign gene. The expression of this gene is activated in human cells in the presence of wild-type HIV. This gene product can cause cell death in the presence of an appropriate drug, e.g. Acyclovir. This gene product is typically a viral thymidine kinase. rHIV is so constructed that it is unable to replicate by itself due to the absence of a regulatory gene that is necessary for its replication, such as tat or rev or both. The recombinant mammalian cell-line packaging system comprises in its genome a recombinant gene construction which typically includes a functional regulatory gene from HIV which is missing from rHIV, such as the tat or rev genes or both. The method for treating infection of cells by HIV comprises administering a composition comprising rHIV, which is produced in vitro from a recombinant mammalian cell-line, and treating with a nucleoside analog, such as Acyclovir or Gancyclovir.

16 Claims, 9 Drawing Sheets

OTHER PUBLICATIONS

A. Adachi et al. "Production of Acquired Immunodeficiency Syndrome–Associated Retrovirus in Human and Nonhuman Cells Transfected with an Infectious Molecular Clone".

N.J. Deacon et al. "Genomic Structure of an Attenuated Quasi Species of HIV–1 from a Blood Transfusion Donor and Recipients" *Science*, v.270. Nov. 10, 1995, pp. 988–991.

Arnold J. Levine *Viruses*. Scientific American Library, 1992. (Chp 4 and 7).

Dr. W. French Anderson, "Gene Therapy for AIDS" *Human Gene Therapy*, 5:149–150, (1994).

Caruso, M. et al., "HIV—triggered killing of booby trapped cells prevents viral spread in an HIV infected cell population," *Bone Marrow Transplant*, vol. 9, suppl., 1, pp. 187–188, 1992.

Y. Hasegawa, et al., "Retroviral transfer of JSV1–TK gene into human lung cancer cell line." *Journal of Molecular Medicine*, 73:107–112, (1995).

Harrison, Gail S., et al. "Activation of a Diphtheria Toxin a Gene by Expression of Human Immunodeficiency Virus–1 Tat and Rev Proteins in Transfected Cells." *Human Gene Therapy*, 2:53–60 (1991).

EPO Search Report sent May 7, 1997.

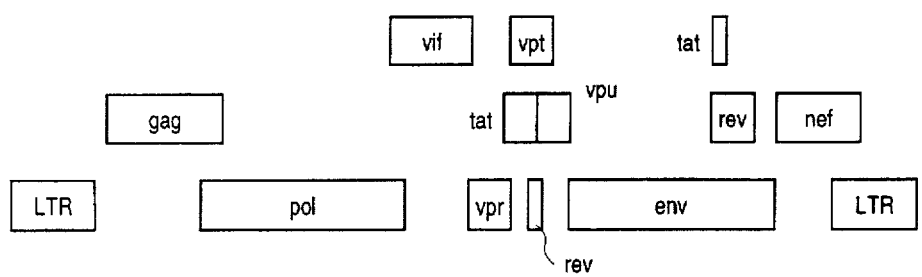
FIG. 2A
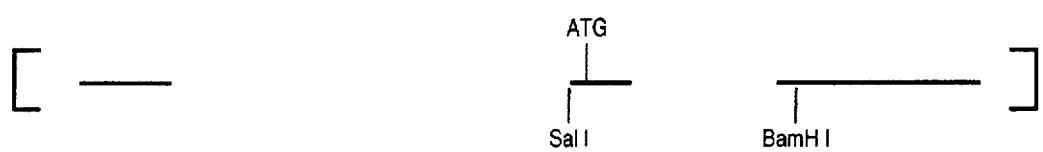
FIG. 2B
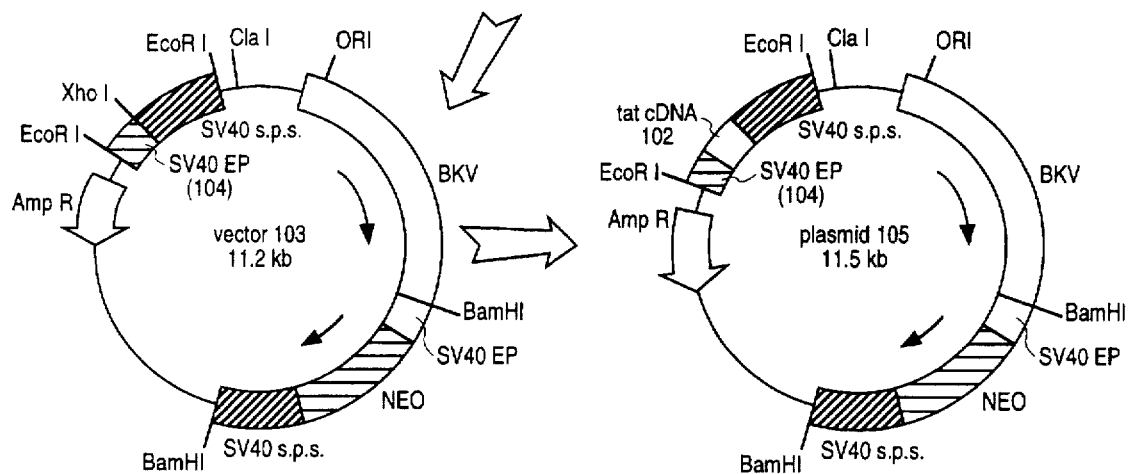
FIG. 2C     FIG. 2D

HIV-1 CONTAINING PLASMID pNL 43

RECOMBINANT HIV AND MODIFIED PACKAGING CELLS AND METHOD FOR TREATING ACQUIRED IMMUNE DEFICIENCY SYNDROME

FIELD OF THE INVENTION

The present invention relates generally to genetic engineering and also to gene therapy wherein a genetically engineered gene is included into a vector for the purposes of in vivo targeted therapy.

BACKGROUND OF THE INVENTION

The availability of genetic engineering, particularly in the form of recombinant DNA technology has increased the possibility of successful gene therapy. A particular desired scenario for gene therapy involves in vivo targeted therapy which is specific for the disease to be treated. Typically, a gene, which expresses a product that is useful in the treatment of the disease, is inserted into a vector, such as a virus, which is then administered to the patient suffering from the disease. There are numerous proposals in the literature for such treatments and vectors.

It will be appreciated that in recent times, considerable effort and resources have been devoted to treating one particular disease in humans which is usually fatal. This disease, acquired immune deficiency syndrome (AIDS) is caused by a particular retrovirus known as human immunodeficiency virus (HIV) which includes the virus known as HIV-1. Numerous treatments for this disease have been proposed and tested and some are currently in use. For example, AIDS is commonly treated by administering the drug AZT to AIDS patients. Moreover, ribozyme and antisense technology are currently being developed as possible treatments for humans suffering from infection by HIV. Many of these new technologies are discussed in volume 260 of SCIENCE, 28 May 1993 issue. As illustrated on page 1257 of this issue of SCIENCE, numerous therapeutics have been identified for various steps in the stages of the replication of HIV. The replication of HIV is attacked by these proposed therapeutics in order to treat the disease. However, it has not been possible to cure the infected individual because of the ability of HIV to remain integrated into the cellular genome and also due to the frequency of changes that appears in the viral genome in every replication cycle.

Often, these various treatments are not permanent and are not economical, and they are often not specific enough. The lack of specificity of the treatments tends to cause complications arising from the effect of the therapeutic drug on uninfected human cells in the body of the patient being treated.

The present invention seeks to provide a novel treatment for AIDS as well as a genetically engineered HIV and a genetically engineered cell line for producing the genetically engineered HIV.

SUMMARY OF THE INVENTION

The invention provides a recombinant human immunodeficiency virus (r HIV) and a recombinant (modified) T-cell line having a functional regulatory gene from HIV, and a method for treating the acquired immune deficiency syndrome in a human caused by HIV.

The modified human immuno deficiency virus (rHIV) includes in its genome a modification (e.g. a deletion) of one of the HIV regulatory genes and the inclusion of a foreign gene. In one embodiment, the foreign gene is a viral kinase enzyme such as a viral thymidine kinase (tk) from the Herpes simplex virus (HSV-1). Typically, the rHIV is unable to express at least one functional regulatory gene product of the genome of HIV because the genome of rHIV has been modified to either remove or incapacitate the gene which encodes this functional regulatory gene product. In one embodiment, this functional regulatory gene product may be either the tat protein or the rev protein of HIV.

The present invention also provides a modified mammalian cell line, such as a modified T-cell line, having in its genome a recombinant gene construction including a gene from the genome of HIV (usually the wild-type HIV-1). This foreign gene will typically encode a functional regulatory gene product of HIV. Typically, this functional regulatory gene product of HIV is the same functional regulatory gene product which the rHIV cannot produce or express. In this fashion, the modified T-cell line will support replication of rHIV while a normal T-cell line (or a normal in vivo T-cell) will not support replication of rHIV. In one embodiment, the modified T-cell line includes the tat gene from wild-type HIV (e.g. HIV-1) and expresses the gene product of this gene so that it becomes possible to replicate rHIV (tat−) in this cell line. This in vitro rHIV production is referred to as a packaging system.

The invention also provides a method for treating AIDS in a human by administering a composition which includes rHIV followed by administering a nucleoside analog. In a typical embodiment, the nucleoside analog is Acyclovir or Gancyclovir. In a typical implementation of this method, the rHIV is harvested from the modified T-cell line. The harvested rHIV will then be administered to the patient suffering from AIDS. rHIV will infect all HIV-1 infectable cells. In one embodiment, the tk gene included in rHIV will be actively expressed only in the presence of wild-type HIV. Treatment with Acyclovir completes this modality.

It will be appreciated that in the preferred embodiment rHIV (typically, rHIV-1) is incapable of replication on its own in a normal T-cell line or a normal T-cell. That is, it requires the modified T-cell line or T-cell having the regulatory gene which is depleted from rHIV-1. It will also be appreciated that rHIV produced according to the invention is highly infectious and has exactly the same host range as wild-type HIV-1. rHIV-1 is capable of super infecting human T-cells previously infected with wild-type HIV-1. Although rHIV-1 is incapable of replicating by itself in a normal cell, it will infect a previously HIV-1 infected cell as well as an HIV-1 infectable cell, but rHIV-1 will not replicate in cells that lack wild-type HIV-1.

In the case of double infection of a cell with HIV-1 and rHIV-1, rHIV-1 is stimulated to replicate and viral thymidine kinase is produced. This enzyme will phosphorylate a nucleoside analog, such as Acyclovir or Gancyclovir, which is a cytotoxic substance that will kill the HIV-1 infected cell. It will be appreciated that normal cellular thymidine kinase phosphorylates the nucleoside analog very minimally with no consequences. Thus, administering these nucleoside analogs is safe and approved (as these analogs have been successfully used to treat HSV-1 infections in humans); that is these drugs have been well tested due to the fact that they have been prescribed for the treatment of herpes viruses. If HIV-1 infects cells previously infected with rHIV-1, viral thymidine kinase is produced and upon treatment with Acyclovir or Gancyclovir or other nucleoside analogs, these dully infected cells would be killed. The problem of developing resistance to these compositions such as Acyclovir or Gancyclovir does not arise because (1) the time for developing a modified tk gene is not available, and (2) fresh inoculation of rHIV can always be administered to circumvent the problem.

It will be appreciated that repeated treatment may be needed to eradicate the HIV infection from infected individuals and prevent future reinfection from within. This direct in vivo gene therapy not only avoids the costs and complications of ex-vivo approaches but has the potential to become a simple out-patient office procedure. The treated patient can go on to other remedial therapies for the correction of other deficits.

BRIEF DESCRIPTION OF THE DRAWINGS

The present invention will be described while referring to the following figures which are presented for purposes of illustration:

FIGS. 2a, 2b, 2c and 2d show various maps which illustrate the construction of the plasmid that is used to produce a modified mammalian cell or cell line according to the present invention.

Chart 1 shows a test for the replication of progeny virus from a T cell line transfected with various gene constructs.

Chart 2 shows results from the infection of mononuclear peripheral blood cells from four normal donors by the progeny virus produced by the modified T-cell lines of the present invention.

DETAILED DESCRIPTION OF THE PRESENT INTENTION

While the present invention will be described by referring to specific examples of gene constructs, nucleoside analogs, foreign genes, and particular cell lines, as well as other details, it will be appreciated that this description is not to be construed in a manner to limit the scope and spirit of the present invention. Moreover, numerous specific details which are well understood by those in art are described briefly so that the present invention is not unnecessarily obscured.

Figure 1:
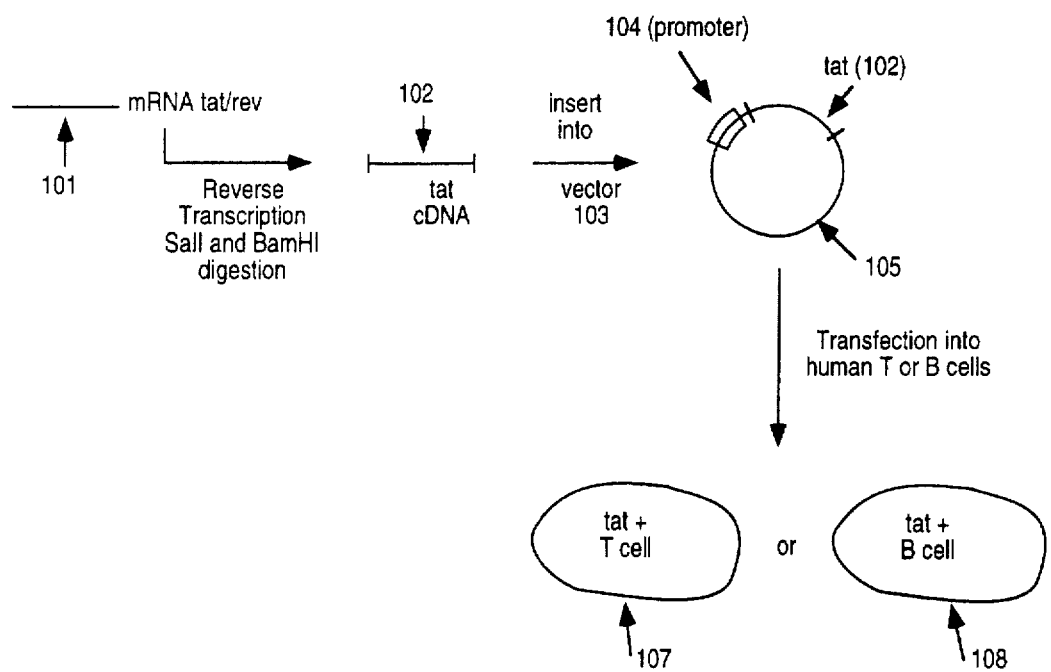
FIG. 1 shows a general method of producing a modified mammalian cell or cell line according to the present invention.

The modified mammalian cell line, such as a modified human T-cell line having in its genome a regulatory gene from wild-type HIV, is created, in one embodiment, according to the general method shown in FIG. 1. In a typical embodiment, the modified cell line will be a human T-cell which is transfected with a plasmid containing an HIV-1 regulatory gene, such as the tat gene, thereby producing a modified T-cell line having the tat gene in its genome. According to the general method shown in FIG. 1, the HIV-1 tat/rev mRNA, labeled 101, is reverse transcribed in order to produce tat/rev cDNA, which is cut with restriction enzymes SalI and BamHI to isolate the two coding exons of HIV-1 tat cDNA, and this product is labelled as 102 in FIG. 1. This tat cDNA is then inserted into a vector 103, typically downstream from a promoter region 104 to produce a resulting plasmid 105 as shown in FIG. 1. This plasmid is then used to transfect human T or B cells (e.g. the Jurkat T cell line) to produce a modified T-cell or a modified B-cell, such as T-cell 107 or B-cell 108. It will be appreciated that other regulatory genes of HIV, such as rev may also be inserted into a plasmid along with the tat gene and this plasmid may then be used to transfect T-cells or B-cells to thereby produce a modified T-cell or B-cell. These cells are typically immortalized cell lines capable of indefinite replication and thus are useful as packaging systems to prepare large numbers of the rHIV-1 described below.

A specific example of this general method shown in FIG. 1 will now be provided in conjunction with FIGS. 2a, 2b, 2c and 2d. FIG. 2a shows a map on the proviral DNA of the genes encoding for the HIV-1 proteins. The two coding exons of the tat gene are indicated by arrows on FIG. 2a. FIG. 2b shows the splicing pattern for the tat/rev mRNA; the SalI and BamHI splicing sites corresponding to the tat cDNA (0.3 kb long) fragment 102 are indicated on the outline of its mRNA shown in FIG. 2b. It will be appreciated that the gaps in the mRNA of FIG. 2b are joined after conventional MRNA post-transcriptional processing. The resulting mRNA tat/rev is shown as fragment 101 in FIG. 1, and this fragment is reverse transcribed as indicated above and then the cDNA is digested with SalI and BamHI to produce the cDNA tat fragment 102, which is 356 base pairs (bp) long and is isolated using conventional techniques.

The expression vector 103, shown in FIG. 1 and FIG. 2c, contains the origin of replication and the early region of the human papavavirus BK (allowing its amplification in human cells), a "cassette" of SV40 early prometer 104, splicing and polyadenylation sequences that permit expression of a CDNA, and plasmid sequences from pBR322. The expression vector 103 also includes the bacterial gene for the aminoglycoside phosphotransferase (Neo) under the control of the SV40 early region promoter and polyadenylation sequences, which confers resistance to the aminoglycoside antibiotic G418 when expressed in euharyotic cells.

The plasmid 105, shown in FIG. 2d, contains the cDNA of HIV-1 tat gene and was derived from plasmid 103, shown in FIG. 2c, in the following manner. The SalI-BamHI fragment 102 of 356 bp (which contains the two coding exons of the HIV-1 tat cDNA) was filled in using the Klenow enzyme (large fragment of DNA polymerase I) and inserted by conventional blunt end ligation into the unique XhoI site of vector 103 which was previously filled in with the Klenow enzyme. This blunt end ligation of the filled in fragment 102 into the vector 103 places the tat cDNA 102 fragment between the SV40 early promoter 104 and the SV40 splicing and polyadenylation signals (shown as SV40 s.p.s. in FIG. 2d).

The Jurkat T-cell is derived from a human T-cell lymphoma and is used in an embodiment where T cells are transfected with the plasmid 105. This transfection produces a modified mammalian T-cell line having tat+ (that is, having the tat gene which expresses functional tat protein).

Plasmid 105 was introduced into these Jurkat T cells by electroporation using conventional electroporators (e.g. from Invitrogen Corporation). In one embodiment, a sample of $10^7$ cells was suspended in 1 ml of the media RPMI 1640 (which is chilled on ice to roughly about 0° C.). Plasmid DNA (in the form of Plasmid 105) was added at concentrations of 100 ng to 1 microgram per sample. Electroporation in a 0.4 cm wide cuvette was carried out at 280 mV and 960 µF. Transfected cells were selected using the antibiotic geneticin (G418). Viable cells were recovered and expanded into cell lines which stably produce the HIV-1 tat protein.

Figure 3:
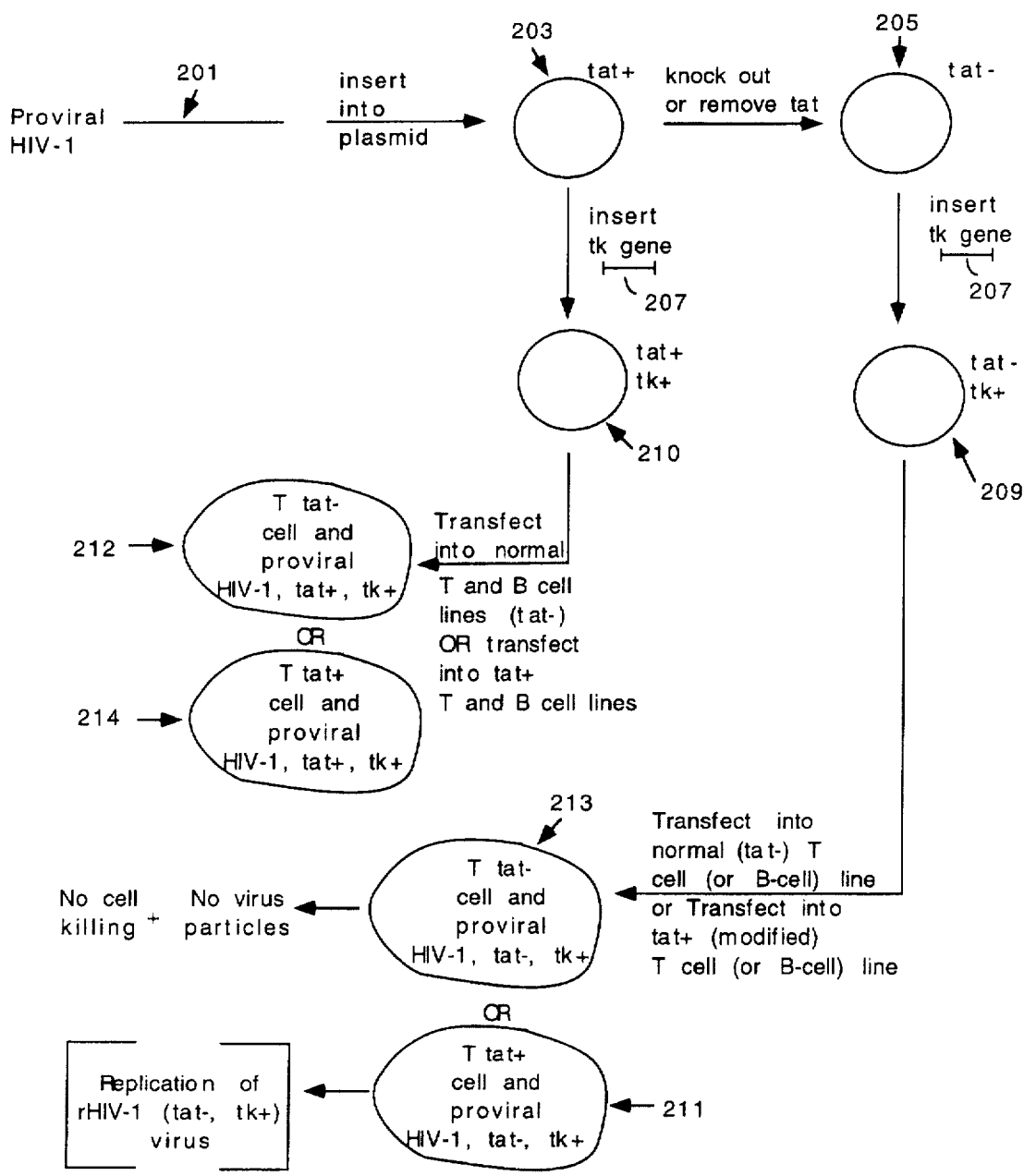
FIG. 3 shows a general method for producing a recombinant HIV and relevant control constructs according to the present invention.

The modified human immunodeficiency virus (e.g. rHIV-1) is produced according to the general method shown in FIG. 3. This method begins with a proviral HIV-1 DNA, labeled 201, which is inserted, using conventional recombinant DNA technology, into a plasmid to create plasmid 203. It will be appreciated that this proviral HIV-1 DNA in one embodiment was constructed from two wild-type HIV and accordingly has the necessary regulatory genes which are essential for its replication. This is not only a replication competent virus, it is also highly infectious. Accordingly, the tat gene will be present in plasmid 203. The plasmid 203 may then be replicated in culture (e.g. in a bacterial culture) to produce a large number of such plasmids using conventional culturing technology. Some of these plasmids may then be harvested for the knock out or removal operation shown in FIG. 3 which creates plasmid 205 from plasmid 203, and similarly some of these plasmids 203 may be harvested for an insertion operation where in the tk gene 207 is inserted into the plasmid 203 to produce the plasmid 210. In an analogous fashion, the plasmid 205 is used to insert the tk gene 207 to produce the plasmid 209. A specific example is given below for incapacitating the tat gene in order to produce the plasmid 205 from the plasmid 203. It will be appreciated by those in the art that the tat gene or other essential regulatory genes may be removed or knocked out in order to render the gene incapable of expressing a functional regulatory gene product. For example, the rev gene may be knocked out in addition to the removal or knock out of the tat gene.

After producing plasmids 210 and 209 from plasmids 203 and 205 respectively, conventional transfection operations are performed in order to introduce the respective plasmid into normal T-cell lines or modified T-cell lines. Alternatively, transfection operations may be performed on normal B-cell lines or modified B-cell lines. Currently, transfection of modified T-cell lines containing the tat gene of HIV-1 (wild-type) is preferred. Given this preference for transfection into T-cell or T-cell lines, this transfection procedure may be carried out as described above. Typically, the electroporation technique is used to cause transfection in order to efficiently introduce the DNA construct into the packaging cells. However, alternative methods of transfection may also be performed. In one embodiment a DNA construct, such as plasmid 209, may be transfected into T-cells (e.g. modified Jurkat tat+ cells) by first cleaving the construct into two pieces (e.g. including a cleavage at the SalI site) and then sequentially introducing (by for example electroporation) one piece into the T-cells and then the other piece into the same T-cells. Then, the T-cells may assemble the pieces to produce a competent cell packaging system (e.g. T-cells 211) which will produce the rHIV of the present invention.

In the case of the plasmid 210 which contains a complete copy of the HIV-1 genome as well as a complete copy of the tk gene (from, for example, HSV-1), this plasmid is transfected into a normal (tat−) T-cell or T-cell line, thereby producing a T-cell 212 having an integrated proviral HIV-1 genome which includes the tk gene from HSV-1. Transfection of a modified (tat+) T-cell or modified T-cell line which contains the tat gene from HIV-1 (wild-type) with plasmid 210 produces a T-cell 214 which contains a integrated proviral copy of the HIV-1 genome with the tk gene as well as a further copy of the tat gene in the genome of the T-cell. It will be appreciated that these modified T-cells are produced according to the method described in conjunction with FIG. 1 above. It will be appreciated that T-cells 212 and T-cells 214 are used as controls in the experiments described below which establish the efficacy of the methods for producing the proper and desired gene constructs and the desired rHIV-1 and modified T-cells/T-cell lines.

Plasmid 209 is also used to transfect both normal T-cells or T-cell lines and modified T-cells or modified T-cell lines. Plasmid 209 contains a full copy of the HIV-1 genome with the exception that a regulatory gene has been disabled or totally removed (e.g. tat−), and it also includes a copy of the tk gene (full functional copy capable of expressing viral thymidine kinase). In the embodiment shown in FIG. 3 the functional regulatory gene of HIV which has been disabled is the tat gene, and thus the plasmid 209 is labeled as "tat−" to indicate the absence of this functional regulatory gene of HIV-1. After producing many copies of the plasmid 209 and harvesting these plasmids from their bacterial host, one sample of plasmids 209 is used to transfect a normal (tat−) T-cell or T-cell line, and another sample of plasmid 209 is used to transfect a modified (tat+) T-cell or T-cell line, thereby producing T-cell 213 or T-cell 211 respectively. The transfection procedures are similar to those described above. The T-cell 213 will be incapable of producing complete HIV-1 viral particles due to the absence of the tat gene on both the genome of the T-cell and the proviral copy of HIV-1 in the genome of the T-cell. These T-cells, such as T-cell 213 may be used as a control in the experiments shown below to establish the efficacy and functionality of rHIV-1 as well as the modified T-cell line. The T-cell 211 will be able to produce multiple viral products, in this case the modified or recombinant human immunodeficiency virus referred to as rHIV-1 which lacks the functional regulatory gene tat and consequently is unable to express the gene product of this gene but does include a copy of the HSV-1 thymidine kinase gene. This viral product may then be used to treat AIDS in the method described below. The T-cell 211 is capable of producing this recombinant virus by virtue of having a separate copy of the tat gene which is expressed by the transcription and translation system of the modified T-cell. That tat gene product expressed in this T-cell 211 allows the proviral HIV-1 having the tk gene (tk+) but not having a functional copy of the regulatory gene tat (tat−) to replicate itself to produce multiple copies of rHIV-1 (tat−, tk+). Thus, T cell 211 may be considered a packaging system for producing this recombinant virus.

It will be appreciated that numerous gene constructs such as the plasmids 203, 205, 209, and 210 may be constructed in various ways to achieve the results described herein. Thus, the specific examples given below for these particular gene constructs are merely one implementation of the present invention. In a particular embodiment of the present invention, plasmid 203 is pNL 43, shown in FIG. 4. In this same embodiment, plasmid 205 is plasmid pNL43dBM, shown partially in FIG. 5, which shows a design strategy for the inactivation of the HIV-1 tat gene. The tk gene insert 207 shown in FIG. 3 is produced in this same embodiment according to the design procedure shown in FIG. 7. The plasmid 209 in this same embodiment, which is the plasmid of interest since it produces rHIV-1 in the modified T-cell line, is the plasmid pNL43dBMtk and is produced according to the design procedure shown in FIG. 6. The control plasmid 210 in this embodiment is known as plasmid pNL43tk.

Figure 8:
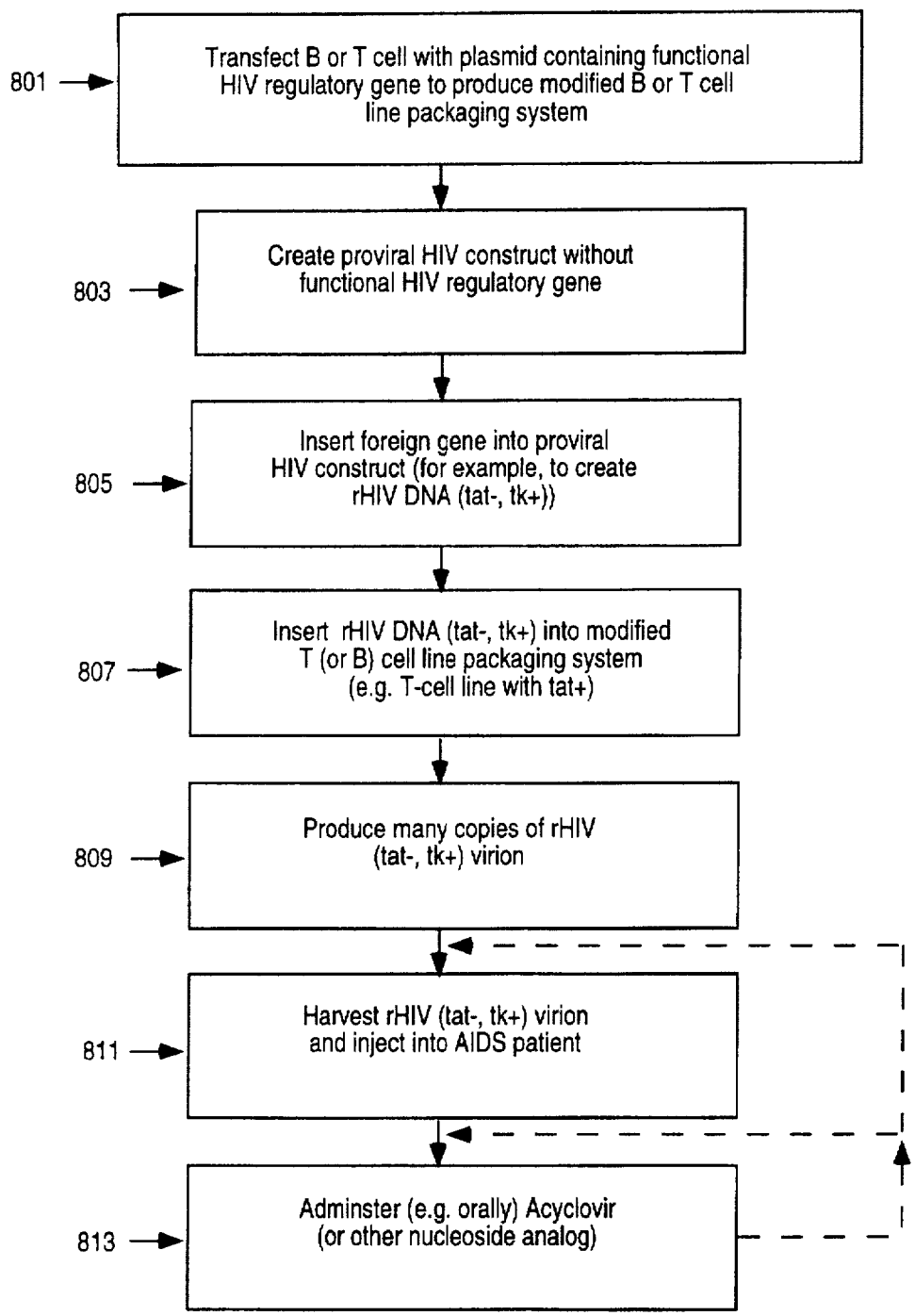
FIG. 8 shows a general method for treating HIV infection with a recombinant HIV, as well as a method for producing the recombinant HIV.
Figure 9:
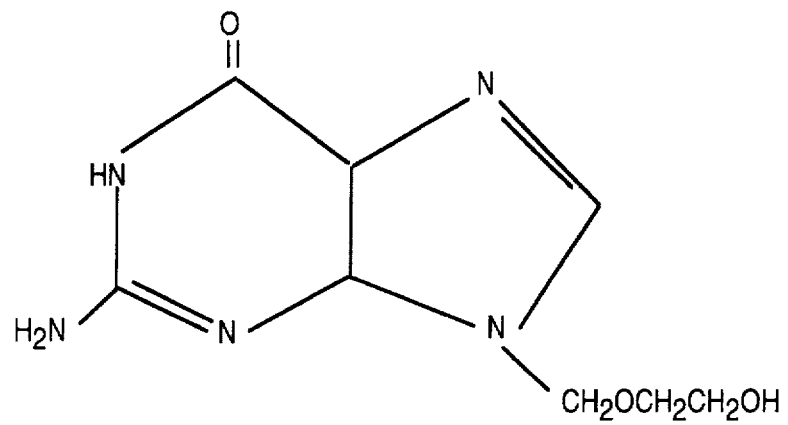
FIG. 9 illustrates the nucleoside analog Acyclovir.

After producing multiple copies of the recombinant HIV, which in the particular embodiment described above is rHIV-1 (tat–, tk+), the treatment of humans infected with HIV-1 may then be performed by administering the recombinant virus and a nucleoside analog to the same patient. This will be described by referring to FIG. 8 which also provides an overview of the invention. While FIG. 8 presents one example of the method according to the present invention, it will be appreciated that certain of the steps (e.g. 801, 803, 805, and 807) may be performed in a sequence which is different from that shown in FIG. 8. The method begins in step 801 wherein a T-cell line (or a B-cell line) is transfected with a plasmid which contains the functional HIV regulatory gene (e.g. tat gene) in order to produce a modified T-cell line which will be the packaging system used to produce the recombinant in HIV of the present invention. In step 803, a proviral HIV construct is created without the functional HIV regulatory gene (e.g. tat gene) which has been inserted into the modified T-cell in step 801. Then in step 805, a foreign gene such as the HSV-1 thymidine kinase gene is inserted into the proviral HIV construct created in step 803. This creates, for example, rHIV-1 (tat–, tk+). Then in step 807, this recombinant DNA [(for example, rHIV-1 (tat–, tk+) DNA] is then inserted into the modified T-cell line packaging system which was created in step 801. This produces in step 809 many copies of the recombinant virus [(for example, rHIV (tat–, tk+)]. Then in step 811, this recombinant virus is harvested and then injected into a human patient suffering from infection by wild-type HIV-1. Alternatively, a sample of the patient's blood may be taken and cultured with the recombinant virus (to infect T cells in the sample) and then the sample is injected back into the patient. Then, in step 813, a nucleoside analog such as Acyclovir is administered orally or Gancyclovir is injected. The standard therapeutic dosages of this nucleoside analog may typically be used several times over a period of time. While administering Acyclovir, blood samples from the patient may be taken to determine the progress of the treatment (by measuring the quantity of HIV present and/or the number of infected cells). As shown by the dashed lines in FIG. 8, further injections of the recombinant virus into the patient may be performed followed by further administrations of the nucleoside analog. Again, the progress of the treatment may be monitored by taking samples of the patient's blood and measuring the quantity of HIV present and/or the number of cells infected by HIV.

A particular implementation of the present invention will now be described by showing particular gene constructs which were used to create an embodiment of the recombinant human immunodeficiency virus of the present invention. FIG. 2a shows a gene map of the proviral form of the HIV-1 genome. As is known, this genome is also similar to the HIV-2 genome and therefore the invention may be used to treat infections by HIV-2. As is known, the tat and rev regulatory genes of HIV-1 are mapped to two non contiguous regions of the genome, and the messenger RNA for tat is a spliced copy of each segment. The inactivation strategy according to the present invention for inactivating tat seeks to disrupt the reading frame of the tat exon.

Figure 4:
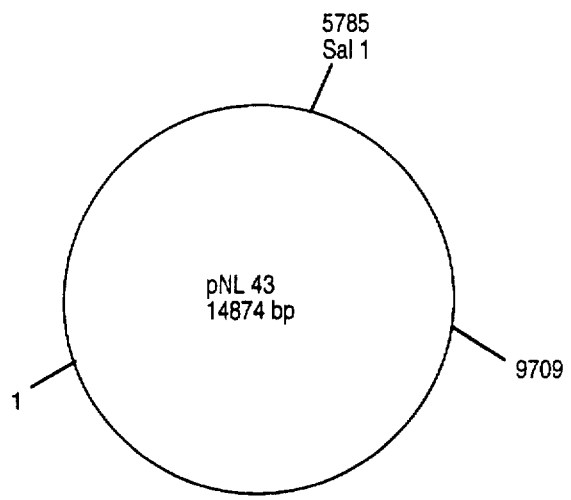
FIG. 4 shows a particular plasmid which is a gene construct containing proviral HIV-1.
Figure 4:
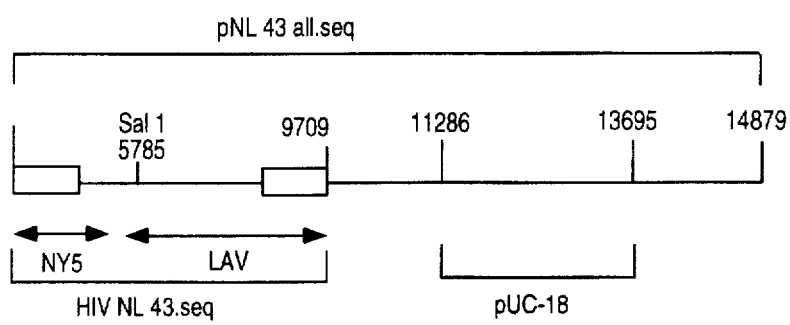

FIG. 4 shows a particular plasmid, the plasmid PNL43 which contains two full copies of HIV from two different isolates of HIV (wild-type). These isolates are referred to as NY5 (5') and LAV (3') an d were cloned directly from genonic DNA. See, generally, Adachi, A., et. al., Journal of Virology, vol. 59, at pages 284–291 (1986). This plasmid pNL43 is used as the basis for the creation of the plasmid pNL43dBM, and the plasmid pNL43dB Mtk.

Figure 5:
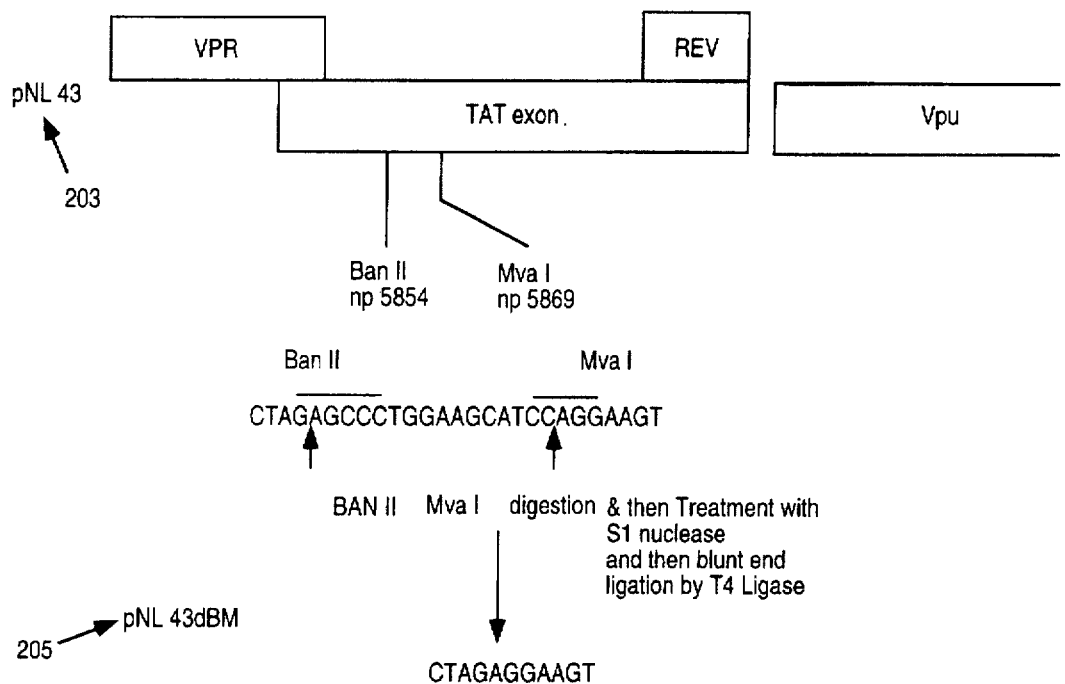
FIG. 5 shows a design strategy for a particular embodiment of the present invention for inactivating a particular regulatory gene of HIV-1.

FIG. 5 shows a design strategy, according to one embodiment, for the HIV-1 (tat–) gene construct, which has been labelled pNL43dBM. The tat gene is inactivated, according to this strategy, by a 16 base pair deletion between BangI and MvaI restriction sites in the HIV-1 proviral DNA. This deletion renders the tat protein functionally inactive. As shown in FIG. 5, the plasmid pNL43dBM (generally represented as plasmid 205 in FIG. 3) is derived from the plasmid pNL43 (which is generally represented as plasmid 203 in FIG. 3). A portion of the HIV-1 DNA in plasmid 203 about 70 nucleotides downstream from the SalI restriction site (in the tat gene) and 25 nucleotides downstream from the ATG codon was cut with BanII and MvaI restriction endonucleases. The fragments were then treated with S1 nuclease to digest the single-stranded portions of the fragments in order to blunt end them. The fragments were then bound to each other by the T4 DNA ligase enzyme. Deletion of the 16 base pair stretch was confirmed by sequencing. Also, see the paper by Shibata, et. al. concerning research on tat mutants; Shibata, R., et. al., Archives of Virology, V. 114, pages 243–250 (1990).

Figure 6:
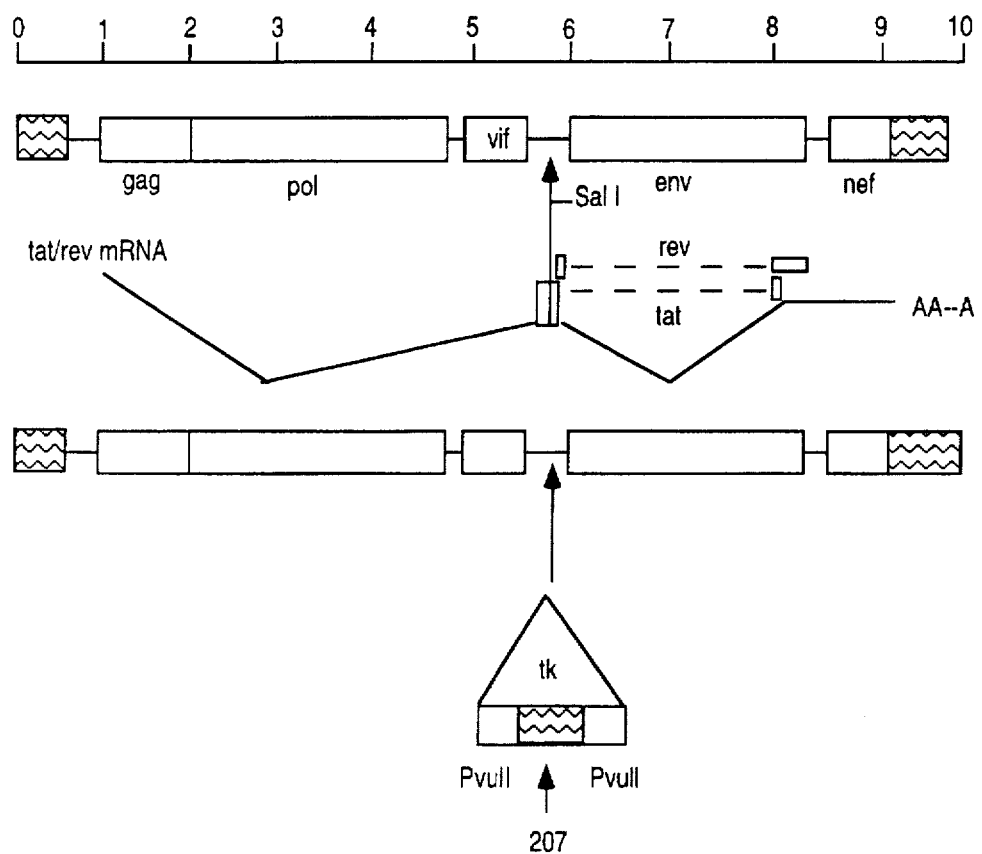
FIG. 6 shows a design strategy for creating a gene construct for rHIV-1 for a particular embodiment of the present invention.
Figure 7:
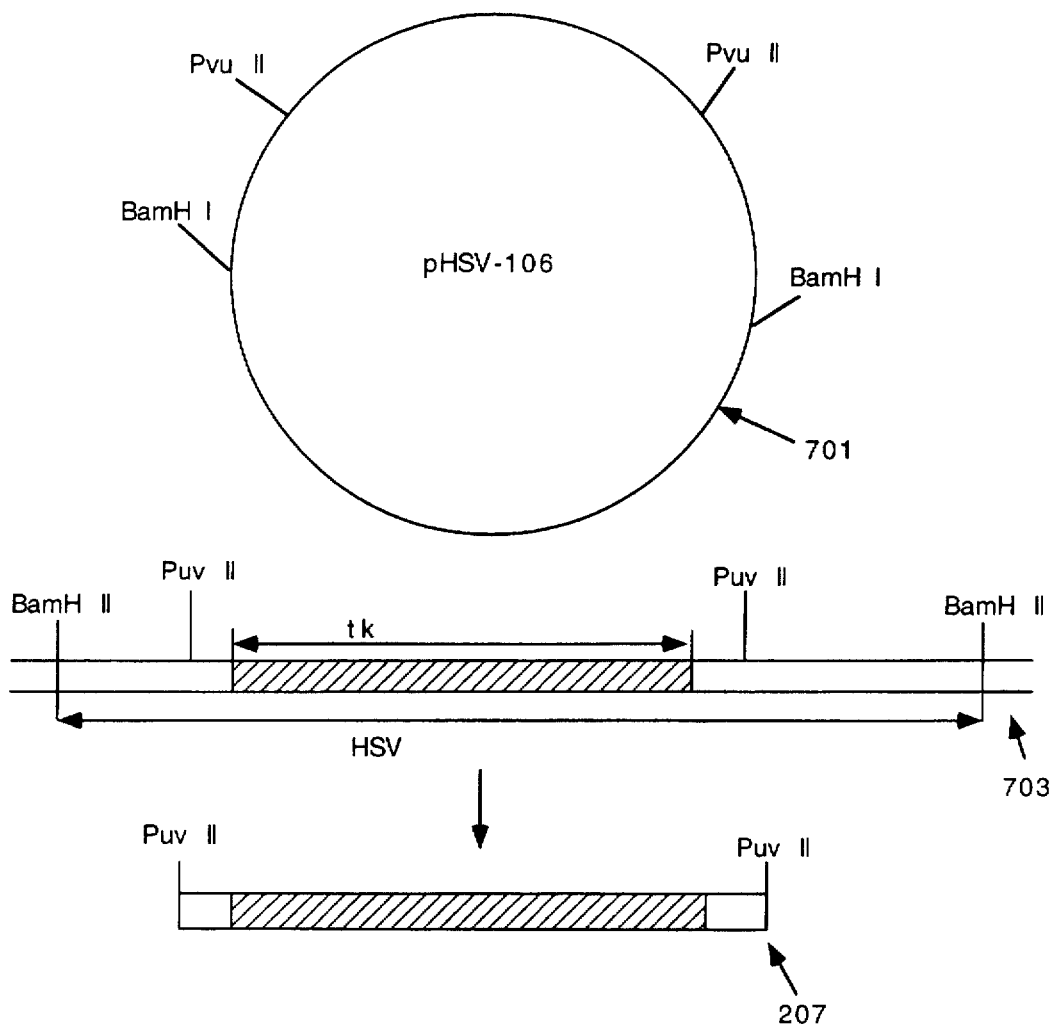
FIG. 7 shows a particular gene construct for a particular embodiment of the present invention; this gene construct contains a foreign gene which is to be inserted into HIV-1 in order to create rHIV-1.

The tk gene from HSV-1 is obtained from the PvuII-PvuII fragment 207 shown in FIG. 7 which may be obtained from the plasmid 701 shown in FIG. 7. In particular in one embodiment, a portion of the HSV-1 genome, containing the tk gene (in the BamHII-BamHII fragment 703), was cloned into a plasmid vector, thus obtaining the plasmid 701. See generally the article by McKnight, S. L. and Grace, E. R., in Nucleic Acid Research, Vol. 8, starting at page 5981 (1980). The PvuII-PvuII fragment 207 shown in FIG. 7 is a fragment containing the complete tk gene that can be expressed under an HIV-1 promoter. This tk fragment 207 is inserted into the HIV proviral genome at the SalI site as shown in FIG. 6. FIG. 6 illustrates a schematic representation of the construction of plasmids 209 and 210 into which the tk fragment is inserted. This insertion is produced by partial digestion by SalI followed by a fill-in reaction to produce blunt ends and the insertion and ligation of the PvuII-PvuII fragment 207. In particular, to make Plasmids 209 and 210, plasmids 203 and 205 respectively were cut with SalI (which is located just after the splice acceptor site for the tat/rev mRNA). The resulting single strand portions of DNA were filled-in with Klenow DNA polymerase producing blunt ends. The PvuII-PvuII fragment 207 of the HSV-1 subclone containing the tk gene (about 2 kilobase pairs in length) was inserted between the blunt ends of opened plasmids 203 and 205 by conventional blunt end ligation.

Charts 1 and 2 illustrate various experimental results which demonstrate the in vitro effectiveness of the treatment method of the present invention and establish and verify the proper construction and functional operation of rHIV-1 (tat–, tk+) and the proper construction and operation of the modified T-cell lines. Chart 1 shows the results of assaying for the presence of p24 (an HIV-1 structural protein), assaying for RT (reverse transcriptase), observing cytopathic effect (CPE) and cell lysis in the presence of Acyclovir. In each case for the Jurkat tat cells (a modified cell-line of human T-cells with tat+), these cells were transfected with one of the three plasmids (pNL43, pNL43tk, or pNL43dBMtk as respectively indicated in rows 3, 4 & 5 of Chart 1) and then the cultures of the respective transfected cells were assayed for p24, RT, CPE and cell lysis (after treatment with 10 microMolar of Acyclovir). It would be expected that the modified T-cells transfected with pNL43BdMtk would produce rHIV-1 (tat–, tk+) and that these cells would experience cell death by lysis from treatments of Acyclovir (due to internal expression of the viral tk gene product). The results shown in chart 1 confirm this expectation as only 13% of the Jurkat (tat+) cells transfected with pNL43dBMtk were positive for HIV-1 p24 after only one treatment. 100% of the control Jurkat (tat+) cells untreated with Acyclovir but transfected with pNL43dBMtk were positive for HIV-1 (not shown in Chart 1). Accordingly some RT and CPE were also detected and observed. Moreover, the same (13%) number survived after cell lysis indicating that cell death by lysis did occur in the presence of Acyclovir. These are the same 13% cells that were present in the IFA test. The potency of pNL43 as an HIV infective carrier is demonstrated by these assays. Control T cells lines (tat–) (i.e. not transformed to include the tat gene) transfected with tat–, tk– (e.g. pNL43dBM) or tat–, tk+ (e.g. pNL43dBMtk) did not synthesize virus-specific antigens and reverse transcriptase was not detected during an extended period of culturing of these control T cell lines.

However, PCR (polymerase chain reaction) analysis did indicate the presence of HIV-1 specific sequences in these control cells, thereby verifying an effective transfection with the plasmids. As shown in Chart 1, the modified Jurkat (tat+) cells supported the production of infectious virus efficiently, including those cells transfected with pNL43, pNL43tk and pNL43dBMtk.

CHART 1

Test of pNL43 transfected Jurkat (tat+) cells for the replication of the progency virus and response to Acyclovir (10 µM)

|  | Primary Transfectant Jurkat (tat+) | | | |
|---|---|---|---|---|
| Specimen Supernatant | IFA p24 (%+) | RT | CPE | Cell Lysis after Acyclovir |
| PBMC Negative | — | – | – | — |
| Jurkat | — | – | – | — |
| pNL43 | 45 | ++ | – | No Effect |
| pNL43tk | 43 | + | –+ | 13 |
| pNL43dBMtk | 13 | + | + | 13 |
| HIV (LAV) | 47 | ++ | – | No Effect |

Chart 2 demonstrates the infectiousness of the various forms of recombinant virus [including both of the control viruses produced by transfection of T-cells with pNL43 and pNL43tk and the desired recombinant virus rHIV-1 (tat–, tk+) produced by transfection of T-cells with pNL43dBMtk]. Note that these recombinant viruses were used for the infection of normal (not infected by HIV) fresh peripheral blood mononuclear cells (PBMC), which are known to be targets of wild-type HIV-1; these cells were also exposed to a wild-type HIV-1 (the HIV-1 LAV isolate) to verify their expected infectability. The PBMC exposed to rHIV-1 (tat–, tk+) were not killed by this virus while those PBMC cells exposed to the control recombinant viruses (shown in the columns pNL43 and pNL43tk) were killed as expected. In the case of the column labeled pNL43dBM, the supernatant from transfected T (tat+) cells (transfected with pNL43dBM) was applied to the culture containing the PBMC cells; it will be appreciated that it would be expected, based on the teachings of this invention, that no virus would be produced in this case, and no infection or cell lysis would occur. This expectation was also confirmed.

CHART 2

Infection of PBMC from 4 normal donors by the progency virus produced by the pNL43 series of virus produced from Jurkat tat+ cells.

| Specimen number | pNL43 | pNL43dBM | pNL43tk | pNL43dBMtk | HIV-1 (LAV) | Uninfected Control |
|---|---|---|---|---|---|---|
| 1 | CPE/cell lysis | no response | CPE/cell lysis | no response | CPE/cell lysis | Good |
| 2 | CPE/cell lysis | no response | CPE/cell lysis | no response | CPE/cell lysis | Good |
| 3 | CPE/cell lysis | no response | CPE/cell lysis | no response | CPE/cell lysis | Good |
| 4 | CPE/cell lysis | no response | CPE/cell lysis | no response | CPE/cell lysis | Good |

For the columns labelled pNL43 and HIV-1 (LAV), CPE were observed in the infected cells within 3 to 5 days and all cells in these cultures died by 12–15 days. For the column labelled pNL43tk, CPE were observed by the 10th day in culture, although many of these cells remained healthy, and these cells were killed by applying 10 microMolar of Acyclovir.

This evidence demonstrates that the insertion of the tk gene is effective in producing cell death in the presence of a nucleoside analog such as Acyclovir or Gancyclovir and yet does not effect normal HIV specificity and infectivity. This also demonstrates that rHIV (tat–, tk+) is effective in infecting and killing T-cells specifically in the presence of the nucleoside analog. This also demonstrates that inactivation of the tat gene will prevent viral replication.

In addition to the uses described herein for the recombinant virus (e.g. rHIV-1), this virus is useful for research and development into the molecular biology of HIV, and it can be used in animal studies for potentiating immune responses. This virus can also be used to test the response of an animal to the virus in a specially developed murine system which is transplanted with human lymphoid organs. These are mice with sever combined immunodeficiency (SCID-hu). Moreover, this virus can be used in regulated gene therapy strategies by adding a therapeutic gene to the rHIV, and injecting this modified rHIV into an animal and regulating over expression by injecting Acyclovir and injecting tat protein to cause expression of the therapeutic gene. The rHIV of the present invention may also be used in research and experimentation in the field of immunosuppression; for example, rHIV may be used to produce immunosuppresion to enhance organ transplantation or may be used to treat autoimmune disorders. In one case, rHIV may be introduced into an organ transplant patient and then the tat gene product may be injected intravenously while Acyclovir is introduced in the patient; in this manner, the infected CD4 lymphocytes may be selectively killed to suppress the immune system.

Various of the plasmids and cell lines described above have been deposited with the American Type Culture Collection (ATCC). In particular, samples of the modified Jurkat (tat+) T cell line have been deposited with the ATCC, 12301 Parklawn Drive, Rockville, Md., U.S.A. on Oct. 3, 1995 under ATCC Accession No. CRL 11987. Samples of the unmodified (control) Jurkat T cell (untransfected with plasmid 105) have been deposited with the ATCC, 12301 Parklawn Drive, Rockville, Md. U.S.A. on Oct. 3, 1995 under ATCC Accession No. CRL 11988. Samples of the plasmids pNL43, in samples contained within *Escherichia coli* bacteria, have been deposited with the ATCC, 12301 Parklawn Drive, Rockville, Md., U.S.A. on Oct. 3, 1995 under ATCC Accession No. 69928. Samples of the plasmid pNL43dBM, contained within bacteria *Escherichia coli*, have been deposited with the ATCC, 12301 Parklawn Drive, Rockville, Md., U.S.A. on Oct. 3, 1995 under ATCC Accession No. 69927. Samples of the plasmid pNL43dBMtk, contained within bacteria *Escherichia coli*, have been deposited with the ATCC, 12301 Parklawn Drive, Rockville, Md., U.S.A. on Oct. 3, 1995 under ATCC Accession No. 69929.

These deposits with the ATCC provide for permanent availability of the progeny of these cell lines to the public on the issuance of the U.S. patent describing and identifying the deposit or the publication or laying open to the public of any U.S. or foreign patent applications, which ever comes first, and for availability of the progeny of these cell lines to one determined by the U.S Commission of Patents and Trademarks to be entitled thereto according to 35 USC Section 122 and the Commissioner's rules pursuant thereto. The owner of the present application has agreed that if the cell lines on deposit should die or be lost or destroyed when cultivated under suitable conditions, they will be promptly replaced on notification with a viable culture of the same cell line.

The present invention is not to be limited in scope by the microorganisms or cells deposited since the deposited embodiment is intended as a single illustration of one aspect of the invention and any microorganisms or cells or modified viruses which are functionally equivalent are within the scope of this invention. Indeed various modifications of the invention in addition to those shown and described herein will become apparent to those skilled in the art from the foregoing description and fall within the scope of the appended claims.

Although the present invention has been described with preferred embodiments, it is to be understood that modifications and variations may be resorted to, without departing from the spirit and scope of this invention, as those skilled in the art will readily understand.

Various forms of the HIV virus may be modified, as described herein, to include the tk gene and to incapacitate the tat gene to produce an rHIV virus of the present invention. A search of the GenBank database may be performed to obtain these HIV viruses. As is well known, the GenBank includes many nucleotide sequences and is maintained by the National Center for Biotechnology Information (National Library of Medicine, National Institutes of Health). The GenBank is available through the home page of the National Center for Biotechnology Information on the World Wide Web (at the Uniform Resource Locator http://www.ncbi.nlm.nih.gov/).

A search of the GenBank for HIV which contain proviral sequences similar to a portion of the pNL43 sequence was performed to obtain examples of forms of HIV which are expected to be compatible with the methods of the present invention such that these forms of HIV may be modified to produce a corresponding form of rHIV. Listed below in the accompanying Sequence Listing are portions of 15 examples of these forms of HIV. The following chart (CHART 3) identifies these particular examples by referring to the GenBank's accession number. The portion of the pNL43 sequence used to search the GenBank is shown in the accompanying Sequence Listing as "M19921" (SEQ.ID No: 1).

CHART 3

| Accession No. | Other Description | SEQ. ID NO. |
| --- | --- | --- |
| M19921 | HIVNL43 | 1 |
| L31963 | HIVTH475A | 2 |
| K03455 | HIVHXB2CG | 3 |
| U12055 | HIV1U12055 | 4 |
| K02013 | HIVBRUCG | 5 |
| M15654 | HIVBH102 | 6 |
| I04549 | European Patent 0187041 | 7 |
| X01762 | REHTLV3 | 8 |
| I07983 | European patent 0185444 | 9 |
| K02083 | HIVPV22 | 10 |
| M17449 | HIVMNCG | 11 |
| I12142 | U.S. Pat. No. 5,420,030 | 12 |
| M38429 | HIVJRCSF | 13 |
| L02317 | HIV1SG3X | 14 |
| N96155 | HIV1PROV | 15 |

We claim:

1. A modified packaged human immunodeficiency virus-1 (modified HIV-1) comprising in its genome a chimeric gene construct including a HSV thymidine kinase gene, said chimeric gene construct being effective in human cells infected with a human immunodeficiency virus-1 (HIV-1) to express HSV thymidine kinase from said HSV thymidine kinase gene, said modified HIV-1 being unable to express at least one functional regulatory gene product of HIV-1 and said modified HIV-1 having a gene which encodes an HIV-1 env protein, and said modified HIV-1 infecting the same host range as wild type HIV-1, and being packaged into viral particles.

2. A modified packaged HIV-1 as in claim 1 wherein said at least one functional regulatory gene product is the tat gene product of the HIV-1 genome.

3. A modified HIV-1, as in claim 2 wherein said modified HIV-1 further comprises the HIV-1 genes vif, gag, pol and nef.

4. A modified HIV-1 as in claim 3 wherein said viral thymidine kinase gene is located in the genome of said modified HIV-1, between said vif gene and said gene which encodes said HIV-1 env protein in the genome of said modified HIV-1.

5. A modified HIV-1 as in claim 4 wherein said modified HIV-1 is unable to replicate in a cell without the presence of a wild-type HIV-1 in said cell.

6. A modified HIV-1 as in claim 5 wherein said tat gene in said modified HIV-1 has a plurality of base deletions between Ban II and Mva I restriction sites in said genome of said modified HIV-1.

7. A method for producing a modified human immunodeficiency virion (modified HIV-1) comprising:

producing a plurality of modified HIV-1 in a modified mammalian cell, said modified HIV-1 having a gene which encodes a HSV-thymidine kinase gene product and being unable to express at least one functional regulatory gene product, said modified mammalian cell having a gene which encodes said at least one functional regulatory gene product.

8. A method as in claim 7 further comprising harvesting said plurality of modified HIV-1 from said modified mammalian cell.

9. A method as in claim 8 wherein said step of producing is performed in tissue culture and wherein said modified mammalian cell is from a human T cell-line.

10. A method as in claim 9 wherein said functional regulatory gene product is a tat protein of a human immunodeficiency virus-1.

11. A modified human immunodeficency virion (modified HIV-1) produced by a process comprising:

culturing a modified mammalian cell, said modified mammalian cell having a gene which encodes at least one functional regulatory gene product of HIV-1;

producing a plurality of modified HIV-1 in said modified mammalian cell, said modified HIV-1 having a gene which encodes HSV thymidine kinase and being unable to express said at least one functional regulatory gene product of HIV-1.

12. A modified HIV-1 produced by a process as in claim 11, wherein prior to culturing said modified mammalian cell, said modified mammalian cell was transfected with a vector containing the genome of said modified HIV-1.

13. A modified HIV-1 produced by a process as in claim 11 further comprising harvesting said plurality of modified HIV-1 from said modified mammalian cell.

14. A modified HIV-1 produced by a process as in claim 11 wherein said modified mammalian cell is from a human T cell line.

15. A modified HIV-1 produced by a process as in claim 11 wherein said at least one functional regulatory gene product of HIV-1 is the tat gene product.

16. A modified HIV-1 produced by a process as in claim 11 wherein said modified HIV-1 is unable to replicate in a mammalian cell without the presence of wild-type HIV-1.

* * * * *

SEQUENCE LISTING ( 1 ) GENERAL INFORMATION:

( i i i ) NUMBER OF SEQUENCES:15

( 2 ) INFORMATION FOR SEQ ID NO:1:

( i ) SEQUENCE CHARACTERISTICS:
  ( A ) LENGTH:351

(B) TYPE:Nucleic acid
(C) STRANDEDNESS:Double-stranded
(D) TOPOLOGY:Unknown (i i) MOLECULE TYPE:
(A) DESCRIPTION:GenBank Accession No: M19921; Human
immunodeficiency virus type 1, NY5/BRU (x i) SEQUENCE DESCRIPTION: SEQ ID NO: 1:

| | | | | | |
|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATGACA | 240 |
| AAAGCCTTAG | GCATCTCCTA | TGGCAGGAAG | AAGCGGAGAC | AGCGACGAAG | AGCTCATCAG | 300 |
| AACAGTCAGA | CTCATCAAGC | TTCTCTATCA | AAGCAGTAAG | TAGTACATGT | A | 351 |

(2) INFORMATION FOR SEQ ID NO: 2:

(i) SEQUENCE CHARACTERISTICS:
(A) LENGTH:351
(B) TYPE:Nucleic acid
(C) STRANDEDNESS:Double-stranded
(D) TOPOLOGY:Unknown (i i) MOLECULE TYPE:
(A) DESCRIPTION:GenBank Accession No: L31963; Human
Immunodeficiency virus type 1 (individ (x i) SEQUENCE DESCRIPTION: SEQ ID NO: 2:

| | | | | | |
|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCAACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | CTTGCTATTG | TAAAAAGTGT | TGCTTTCATT | GCCAAGTTTG | TTTCATGACA | 240 |
| AAAGCCTTAG | GCATCTCCTA | TGGCAGGAAG | AAGCGGAGAC | AGCGACGAAG | AGCTCATCAG | 300 |
| AACAGTCAGA | CTCATCAAGC | TTCTCTATCA | AAGCAGTAAG | TAGTACATGT | A | 351 |

(2) INFORMATION FOR SEQ ID NO: 3:

(i) SEQUENCE CHARACTERISTICS:
(A) LENGTH:351
(B) TYPE:Nucleic acid
(C) STRANDEDNESS:Double-stranded
(D) TOPOLOGY:Unknown (i i) MOLECULE TYPE:
(A) DESCRIPTION:GenBank Accession No: K03455; Human
immunodeficiency virus type 1 (HXB2), (x i) SEQUENCE DESCRIPTION: SEQ ID NO: 3:

| | | | | | |
|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | AGCTCATCAG | 300 |
| AACAGTCAGA | CTCATCAAGC | TTCTCTATCA | AAGCAGTAAG | TAGTACATGT | A | 351 |

(2) INFORMATION FOR SEQ ID NO: 4:

(i) SEQUENCE CHARACTERISTICS:

( A ) LENGTH:351
( B ) TYPE:Nucleic acid
( C ) STRANDEDNESS:Double- stranded
( D ) TOPOLOGY:Unknown ( i i ) MOLECULE TYPE:
( A ) DESCRIPTION:GenBank Accession No: U12055; Human
immunodeficiency virus type 1 isolate ( x i ) SEQUENCE DESCRIPTION: SEQ ID NO: 4:

| GGGATACTTG | GGCAGGAGTG | GAAGCCATAA | TAAGAATTCT | GCAACAACTG | CTGTTTACCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCT | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | ACCTCCTCAA | 300 |
| AGCAGTCAGA | CTCATCAAGT | TTCTCTATCA | AAGCAGTAAG | TAGTACATGT | A | 351 |

( 2 ) INFORMATION FOR SEQ ID NO: 5:

( i ) SEQUENCE CHARACTERISTICS:
( A ) LENGTH:351
( B ) TYPE:Nucleic acid
( C ) STRANDEDNESS:Double- stranded
( D ) TOPOLOGY:Unknown ( i i ) MOLECULE TYPE:
( A ) DESCRIPTION:GenBank Accession No: K02013; Human
immunodeficiency virus type 1, isolate ( x i ) SEQUENCE DESCRIPTION: SEQ ID NO: 5:

| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCAACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | CTTGCTATTG | TAAAAAGTGT | TGCTTTCATT | GCCAAGTTTG | TTTCACAACA | 240 |
| AAAGCCTTAG | GCATCTCCTA | TGGCAGGAAG | AAGCGGAGAC | AGCGACGAAG | ACCTCCTCAA | 300 |
| GGCAGTCAGA | CTCATCAAGT | TTCTCTATCA | AAGCAGTAAG | TAGTACATGT | A | 351 |

( 2 ) INFORMATION FOR SEQ ID NO: 6:

( i ) SEQUENCE CHARACTERISTICS:
( A ) LENGTH:351
( B ) TYPE:Nucleic acid
( C ) STRANDEDNESS:Double- stranded
( D ) TOPOLOGY:Unknown ( i i ) MOLECULE TYPE:
( A ) DESCRIPTION:GenBank Accession No: M15654; Human
immunodeficiency virus type 1, isolate ( x i ) SEQUENCE DESCRIPTION: SEQ ID NO: 6:

| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | ACCTCCTCAA | 300 |
| GGCAGTCAGA | CTCATCAAGT | TTCTCTATCA | AAGCAGTAAG | TAGTACATGT | A | 351 |

( 2 ) INFORMATION FOR SEQ ID NO: 7:

( i ) SEQUENCE CHARACTERISTICS:
            ( A ) LENGTH:351
            ( B ) TYPE:Nucleic acid
            ( C ) STRANDEDNESS:Double- stranded
            ( D ) TOPOLOGY:Unknown ( i i ) MOLECULE TYPE:
            ( A ) DESCRIPTION:GenBank Accession No: I04549; Sequence 11
                from patent EP 0187041

( x i ) SEQUENCE DESCRIPTION: SEQ ID NO: 7:

| | | | | | | |
|---|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 1 2 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | ACCTCCTCAA | 300 |
| GGCAGTCAGA | CTCATCAAGT | TTCTCTATCA | AAGCAGTAAG | TAGTACATGT | A | 351 |

( 2 ) INFORMATION FOR SEQ ID NO: 8:

( i ) SEQUENCE CHARACTERISTICS:
            ( A ) LENGTH:351
            ( B ) TYPE:Nucleic acid
            ( C ) STRANDEDNESS:Double- stranded
            ( D ) TOPOLOGY:Unknown ( i i ) MOLECULE TYPE:
            ( A ) DESCRIPTION:GenBank Accession No: X01762; Human T-cell
                leukemia type III (HTLV-III) pr ( x i ) SEQUENCE DESCRIPTION: SEQ ID NO: 8:

| | | | | | | |
|---|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | ACCTCCTCAA | 300 |
| GGCAGTCAGA | CTCATCAAGT | TTCTCTATCA | AAGCAGTAAG | TAGTACATGT | A | 351 |

( 2 ) INFORMATION FOR SEQ ID NO: 9:

( i ) SEQUENCE CHARACTERISTICS:
            ( A ) LENGTH:351
            ( B ) TYPE:Nucleic acid
            ( C ) STRANDEDNESS:Double- stranded
            ( D ) TOPOLOGY:Unknown ( i i ) MOLECULE TYPE:
            ( A ) DESCRIPTION:GenBank Accession No: I079083; Sequence 1
                from patent EP 0185444

( x i ) SEQUENCE DESCRIPTION: SEQ ID NO: 9:

| | | | | | | |
|---|---|---|---|---|---|---|
| GGGATACTTG | GGCAGGAGTG | GAAGCCATAA | TAAGAATTCT | GCAACAACTG | CTGTTTATCC | 60 |
| ATTTCAGAAT | TGGGTGTCGA | CATAGCAGAA | TAGGCGTTAC | TCGACAGAGG | AGAGCAAGAA | 120 |
| ATGGAGCCAG | TAGATCCTAG | ACTAGAGCCC | TGGAAGCATC | CAGGAAGTCA | GCCTAAAACT | 180 |
| GCTTGTACCA | ATTGCTATTG | TAAAAAGTGT | TGCTTTCATT | GCCAAGTTTG | TTTCATAACA | 240 |
| AAAGCCTTAG | GCATCTCCTA | TGGCAGGAAG | AAGCGGAGAC | AGCGACGAAG | ACCTCCTCAA | 300 |
| GGCAGTCAGA | CTCATCAAGT | TTCTCTATCA | AAGCAGTAAG | TAGTACATGT | A | 351 |

( 2 ) INFORMATION FOR SEQ ID NO: 10:

( i ) SEQUENCE CHARACTERISTICS:
    ( A ) LENGTH:351
    ( B ) TYPE:Nucleic acid
    ( C ) STRANDEDNESS:Double- stranded
    ( D ) TOPOLOGY:Unknown ( i i ) MOLECULE TYPE:
    ( A ) DESCRIPTION:GenBank Accession No: K02083; Human immunodeficiency virus type 1, isolate ( x i ) SEQUENCE DESCRIPTION: SEQ ID NO: 10:

```
GGGATACTTG GGCAGGAGTG GAAGCCATAA TAAGAATTCT GCAACAACTG CTGTTTATCC      60
ATTTCAGAAT TGGGTGTCGA CATAGCAGAA TAGGCGTTAC TCGACAGAGG AGAGCAAGAA     120
ATGGAGCCAG TAGATCCTAG ACTAGAGCCC TGGAAGCATC CAGGAAGTCA GCCTAAAACT     180
GCTTGTACCA ATTGCTATTG TAAAAAGTGT TGCTTTCATT GCCAAGTTTG TTTCATAACA     240
AAAGCCTTAG GCATCTCCTA TGGCAGGAAG AAGCGGAGAC AGCGACGAAG ACCTCCTCAA     300
GGCAGTCAGA CTCATCAAGT TTCTCTATCA AAGCAGTAAG TAGTACATGT A              351
```

( 2 ) INFORMATION FOR SEQ ID NO: 11:

( i ) SEQUENCE CHARACTERISTICS:
    ( A ) LENGTH:351
    ( B ) TYPE:Nucleic acid
    ( C ) STRANDEDNESS:Double- stranded
    ( D ) TOPOLOGY:Unknown ( i i ) MOLECULE TYPE:
    ( A ) DESCRIPTION:GenBank Accession No: M17449; HIV-1, isolate MN ( x i ) SEQUENCE DESCRIPTION: SEQ ID NO: 11:

```
GGGATACTTG GGCAGGAGTG GAAGCCATAA TAAGAATTCT ACAACAACTG CTGTTTATTC      60
ATTTCAGAAT TGGGTGTCGA CATAGCAGAA TAGGCATTAT TCGACAGAGG AGAGCAAGAA     120
ATGGAGCCAG TAGATCCTAG ACTAGAGCCC TGGAAGCATC CAGGAAGTCA GCCTAAGACT     180
GCTTGTACCA CTTGCTATTG TAAAAAGTGT TGCTTTCATT GCCAAGTTTG TTTCACAAAA     240
AAAGCCTTAG GCATCTCCTA TGGCAGGAAG AAGCGGAGAC AGCGACGAAG AGCTCCTGAA     300
GACAGTCAGA CTCATCAAGT TTCTCTACCA AAGCAGTAAG TAGTACATGT A              351
```

( 2 ) INFORMATION FOR SEQ ID NO: 12:

( i ) SEQUENCE CHARACTERISTICS:
    ( A ) LENGTH:351
    ( B ) TYPE:Nucleic acid
    ( C ) STRANDEDNESS:Double- stranded
    ( D ) TOPOLOGY:Unknown ( i i ) MOLECULE TYPE:
    ( A ) DESCRIPTION:GenBank Accession No: I12142; Sequence 1 from U.S. Patent No. 5,420,030.

( x i ) SEQUENCE DESCRIPTION: SEQ ID NO: 12:

```
GGGATACTTG GGCAGGAGTG GAAGCCATAA TAAGAATTCT ACAACAACTG CTGTTTATTC      60
ATTTCAGAAT TGGGTGTCGA CATAGCAGAA TAGGCATTAT TCGACAGAGG AGAGCAAGAA     120
ATGGAGCCAG TAGATCCTAG ACTAGAGCCC TGGAAGCATC CAGGAAGTCA GCCTAAGACT     180
GCTTGTACCA CTTGCTATTG TAAAAAGTGT TGCTTTCATT GCCAAGTTTG TTTCACAAAA     240
AAAGCCTTAG GCATCTCCTA TGGCAGGAAG AAGCGGAGAC AGCGACGAAG AGCTCCTGAA     300
GACAGTCAGA CTCATCAAGT TTCTCTACCA AAGCAGTAAG TAGTACATGT A              351
```

( 2 ) INFORMATION FOR SEQ ID NO: 13:

( i ) SEQUENCE CHARACTERISTICS:
        ( A ) LENGTH:351
        ( B ) TYPE:Nucleic acid
        ( C ) STRANDEDNESS:Double- stranded
        ( D ) TOPOLOGY:Unknown ( i i ) MOLECULE TYPE:
        ( A ) DESCRIPTION:GenBank Accession No: M38429; Human
        immunodeficiency virus type 1, isolate ( x i ) SEQUENCE DESCRIPTION: SEQ ID NO: 13:

```
GGGATACTTG  GGCAGGAGTG  GAAGCCATAA  TAAGAATACT  GCAACAGCTG  CTGTTTATTC    60
ATTTCAGAAT  TGGGTGTCGA  CATAGCAGAA  TAGGCATTAC  TCGACAGAGG  AGAGCAAGAA   120
ATGGAGCCAG  TAGATCCTAG  CCTAGAGCCC  TGGAAGCATC  CAGGAAGTCA  GCCTAAGACT   180
GCTTGTACCA  ATTGCTATTG  TAAAAAGTGT  TGCCTTCATT  GCCAAGTTTG  TTTCACAACA   240
AAAGGCTTAG  GCATCTCCTA  TGGCAGGAAG  AAGCGGAGAC  AGCGACGAAG  ACCTCCTCAA   300
GACAGTCAGA  CTCATCAAGT  TTCTCTACCA  AAGCAGTAAG  TAGTGCATGT  A            351
```

( 2 ) INFORMATION FOR SEQ ID NO: 14:

( i ) SEQUENCE CHARACTERISTICS:
        ( A ) LENGTH:351
        ( B ) TYPE:Nucleic acid
        ( C ) STRANDEDNESS:Double- stranded
        ( D ) TOPOLOGY:Unknown ( i i ) MOLECULE TYPE:
        ( A ) DESCRIPTION:GenBank Accession No: L02317; Human
        immunodeficiency virus type 1

( x i ) SEQUENCE DESCRIPTION: SEQ ID NO: 14:

```
GGGATACTTG  GGCAGGAGTG  GAAGCCCTAG  TAAGAACTCT  GCAACAACTG  CTGTTTACTC    60
TTTTCAGAAT  TGGGTGTCGA  CATAGCAGAA  TAGGCATTAC  TCAACGAAGA  AGAGCAAGAA   120
ATGGAGCCAG  TAGATCCTAG  ACTAGAGCCC  TGGAAGCATC  CAGGAAGCCA  GCCTAAAACT   180
GCTTGTACCA  AATGCTATTG  TAAAAAGTGT  TGCTTACATT  GCCAAGTTTG  TTTCATGACA   240
AAAGGCTTAG  GCATCTCCTA  TGGCAGGAAG  AAGCGGAGAC  AGCGACGAAG  AGCTCCTCAA   300
GACAGTCAGA  CTCATCAAGC  TTCTCTATCA  AAGCAGTAAG  TAGTGCATGT  A            351
```

( 2 ) INFORMATION FOR SEQ ID NO: 15:

( i ) SEQUENCE CHARACTERISTICS:
        ( A ) LENGTH:351
        ( B ) TYPE:Nucleic acid
        ( C ) STRANDEDNESS:Double- stranded
        ( D ) TOPOLOGY:Unknown ( i i ) MOLECULE TYPE:
        ( A ) DESCRIPTION:GenBank Accession No: M96155; Human
        immunodeficiency virus type 1 proviral ( x i ) SEQUENCE DESCRIPTION: SEQ ID NO: 15:

```
GGGATACTTG  GACAGGAGTG  GAAGCCTTAA  TAAGAATTCT  GCAACAACTG  CTGTTTATTC    60
ATTTCAGAAT  TGGGTGTCGA  CATAGCAGAA  TAGGCATTAT  TCAACACAGG  AGAACAAGAA   120
ATGGAGCCAG  TAAATCCTAG  CCTAGAGCCC  TGGAAGCATC  CAGGAAGTCA  GCCTAAAACT   180
GCTTGTACCA  ATTGCTATTG  CAAAAAATGT  TGCTTTCATT  GCCAAGCTTG  TTTCATAACA   240
AAAGGCTTAG  GCATCTCCTA  TGGCAGGAAG  AAGCGGAGAC  AGCGACGAAG  ACCTCCTCAA   300
GACAGTCAGA  CTCATCAAGT  TTCTCTATCA  AAGCAGTAAG  TAGTACATGT  A            351
```